United States Patent [19]
Jalink, Jr. et al.

[11] Patent Number: 5,844,242
[45] Date of Patent: Dec. 1, 1998

[54] DIGITAL MAMMOGRAPHY WITH A MOSAIC OF CCD ARRAYS

[75] Inventors: Antony Jalink, Jr.; James A. McAdoo, both of Newport News, Va.

[73] Assignee: The United States of America as represented by the Administrator of the National Aeronautics and Space Administration, Washington, D.C.

[21] Appl. No.: 601,143

[22] Filed: Jan. 26, 1996

[51] Int. Cl.[6] ................................................. G01N 23/04
[52] U.S. Cl. ...................................... 250/370.09; 378/37
[58] Field of Search ......................... 250/370.09; 378/37, 378/98.12

[56] References Cited

U.S. PATENT DOCUMENTS

5,142,557  8/1992  Toker et al. ............................... 378/37
5,485,500  1/1996  Baba et al. ............................. 378/98.12

*Primary Examiner*—Edward P. Westin
*Assistant Examiner*—Richard Hanig
*Attorney, Agent, or Firm*—Kimberly A. Chasteen

[57] ABSTRACT

A digital mammography device uses a mosaic of electronic digital imaging arrays to scan an x-ray image. The mosaic of arrays is repositioned several times to expose different portions of the image, until the entire image is scanned. The data generated by the arrays during each exposure is stored in a computer. After the final exposure, the computer combines data of the several partial images to produce a composite of the original x-ray image. An aperture plate is used to reduce scatter and the overall exposure of the patient to x-rays.

26 Claims, 4 Drawing Sheets

DIGITAL MAMMOGRAPHY WITH A MOSAIC OF CCD ARRAYS

ORIGIN OF THE INVENTION

The invention described herein was made by an employee of the U.S. Government and may be manufactured and used by or for the Government for governmental purposes without the payment of any royalties thereon or therefor.

BACKGROUND OF THE INVENTION

1. Technical Field of the invention

The present invention relates generally to a mammography device and method and more particularly to a novel digital mammography device and method to detect microcalcifications of precancerous tissue.

2. Description of the related art

Diagnostic criteria require that mammograms exhibit excellent spatial resolution and contrast sensitivity. X-ray mammography is currently performed by using a conventional phosphor screen film combination as the image receptor. Properly exposed film mammograms can reveal dense precancerous tissue. However, the size of the smallest detectable calcifications, which are indicative of malignancy, is typically about 0.2 mm.

An imaging system which offers wider dynamic range, higher contrast sensitivity, higher spatial resolution, and the ability to manipulate and archive the image is desirable. Digital x-ray mammography can provide the solution to this problem by providing an advanced method and device for diagnosing minimal breast cancers. This digital system can allow for precise identification of microcalcifications, the tiny hardenings typically 0.1 to 0.2 mm in diameter found in precancerous breast tissue.

The large image size (typically 18×24 cm for clinical mammography) could, in principle, be achieved with grazing-incidence-reflection imaging systems in conjunction with existing small-area imaging array detectors. However their bulk and enormous cost make them unsuitable for clinical mammography applications.

Two approaches are currently under investigation for digital mammography.

One is the secondary digitization technique, in which conventional film mammograms are digitized. The other approach is the acquisition of primary digital images, the "electronic imaging technique". There are numerous studies addressing the technical challenges of digital radiography which may be adapted for mammography, examples are: scanning laser stimulated luminescence system, i.e., computed radiography (J. W. Oestmann, D. Kopans, and D. A. Hall, "A comparison of digitized storage phosphors and conventional mammography in the detection of malignant microcalcifications," *Invest. Radiol.*, vol. 23, no. 725, 1988); slot scanning digital imaging, including the TDI technique (Maidment et al., "Scanned-slot mammography," *SPIE Proc.*, vol. 1231, Medical Imaging IV: Image Formation, p. 316, 1990), large size flat panel detectors such as amorphous silicon and selenium detectors (Rowlands, et al., "X-Ray imaging using amorphous selenium: A photoinduced discharge readout method for digital mammography," *Med. Phys.*, vol. 18, pp. 421–431, 1991); and optically coupled electronic imager (e.g., CCD) techniques (H. Liu, A. Karellas, S. C. Moore, and L. J. Harris, "Lesion detectability considerations for an optically coupled CCD x-ray imaging system," *IEIE Trans. Nucl. Sci.*, vol. 41, no. 4, pp. 1506–1509, August 1994).

In U.S. Pat. No. 5,105,087, issued to Jagielinski, incorporated by reference herein, multiple detector arrays are used to image over the large area needed in clinical mammography applications. This invention relies on multiple layers of detector elements, one above the other, to provide a complete image with no gaps. One disadvantage with this system is that enough photo detectors must be used to cover the active area which increases the cost of the device. Another disadvantage is the effect of the edges of the detector arrays in one layer on the x-ray image seen by the detectors below these edges. The present invention is able to use a fewer number of detectors by repositioning the detectors several times in order to cover the entire active area. Thus, the cost of the system is greatly reduced.

In U.S. Pat. No. 5,043,582 issued to Cox et al., incorporated by reference herein, the photo sensitive properties of transistors found in dynamic random access memory (DRAM) integrated circuits are used to detect photons emitted from x-ray sensitive phosphors. The use of DRAM cells as photo sensitive pixels results in less optical sensitivity, because the entire active area of each pixel is not photo sensitive, due to the requirements for addressing the DRAM cells. Furthermore, the detection scheme described by Cox et al. is binary in nature. Therefore, substantial effort would be required to obtain gray scales.

The present invention uses CCD detectors, which are optimized for use as photo detectors. This results in greater system sensitivity and image quality. Also, CCDs produce gray scales naturally and with high sensitivity.

Optically coupled CCD techniques are described in two U.S. patents. In U.S. Pat. Nos. 5,142,557 issued to Toker et al., and 5,216,250 issued to Pellegrino et al., incorporated by reference herein, an optical lens is used to image the visible photons emitted by an x-ray sensitive phosphor screen onto a single CCD detector. Because the CCD detector is smaller than the phosphor screen, the image from the screen must be reduced, or demagnified, in order for the detector to record the entire image. This means that each pixel on the CCD detector corresponds to a larger equivalent area on the phosphor screen. Therefore, the spatial resolution of this system is less than the spatial resolution of the CCD detector. Also, using an optical lens to couple the image on the phosphor screen to the CCD detector is inefficient. The optical lens cannot collect all of the light that is emitted by the phosphor screen. This results in a reduction in signal-to-noise performance.

The present invention is able to achieve an increased spatial resolution because each region on the phosphor screen corresponds to a pixel area on the CCD. In addition, the present invention does not use an optical lens. Therefore, the coupling losses associated with imaging optics are eliminated. This results in higher quality images and less patient dose of x-rays compared to alternate approaches.

SUMMARY OF THE INVENTION

An object of this invention is to provide a digital mammography device with large field coverage.

Another object of this invention is to provide a digital mammography device with high spatial resolution.

Another object of this invention is to provide a digital mammography device with scatter rejection.

Another object of this invention is to provide a digital mammography device with excellent contrast characteristics and lesion detectability under clinical conditions.

Another object of this invention is to provide a mammography device which shields the patient from excessive radiation.

Another object of this invention is to provide a mammography device which can detect extremely small calcifications.

Is Another object of this invention is to provide a mammography device which can manipulate and archive the image.

These and other objects of the invention are met by providing an apparatus and method for large field digital mammography. The invention uses a mosaic of electronic digital imaging arrays to scan an image. The imaging arrays are mounted on a carrier platform to form a pattern. The arrays are then exposed to a portion of a radiated image, and convert this radiation into digital data. The platform is subsequently repositioned and the arrays are exposed to another portion of the image. While the arrays are being repositioned, the digital data in the arrays is transferred to a computer memory. This process is repeated until the entire image has been exposed to the arrays. The stored multiple image data is combined by a data processor to form data which corresponds to the original radiated image. This digital x-ray image can then be viewed on a computer display. To reduce exposure and x-ray scatter, a metallic aperture plate is interposed between the x-ray source and the patient. The aperture plate has a mosaic of square holes in alignment with the imaging array pattern. The plate is repositioned in synchronism with the carrier platform. The device is suitable for incorporation into standard mammography units.

DETAILED DESCRIPTION OF THE INVENTION

Figure 1:
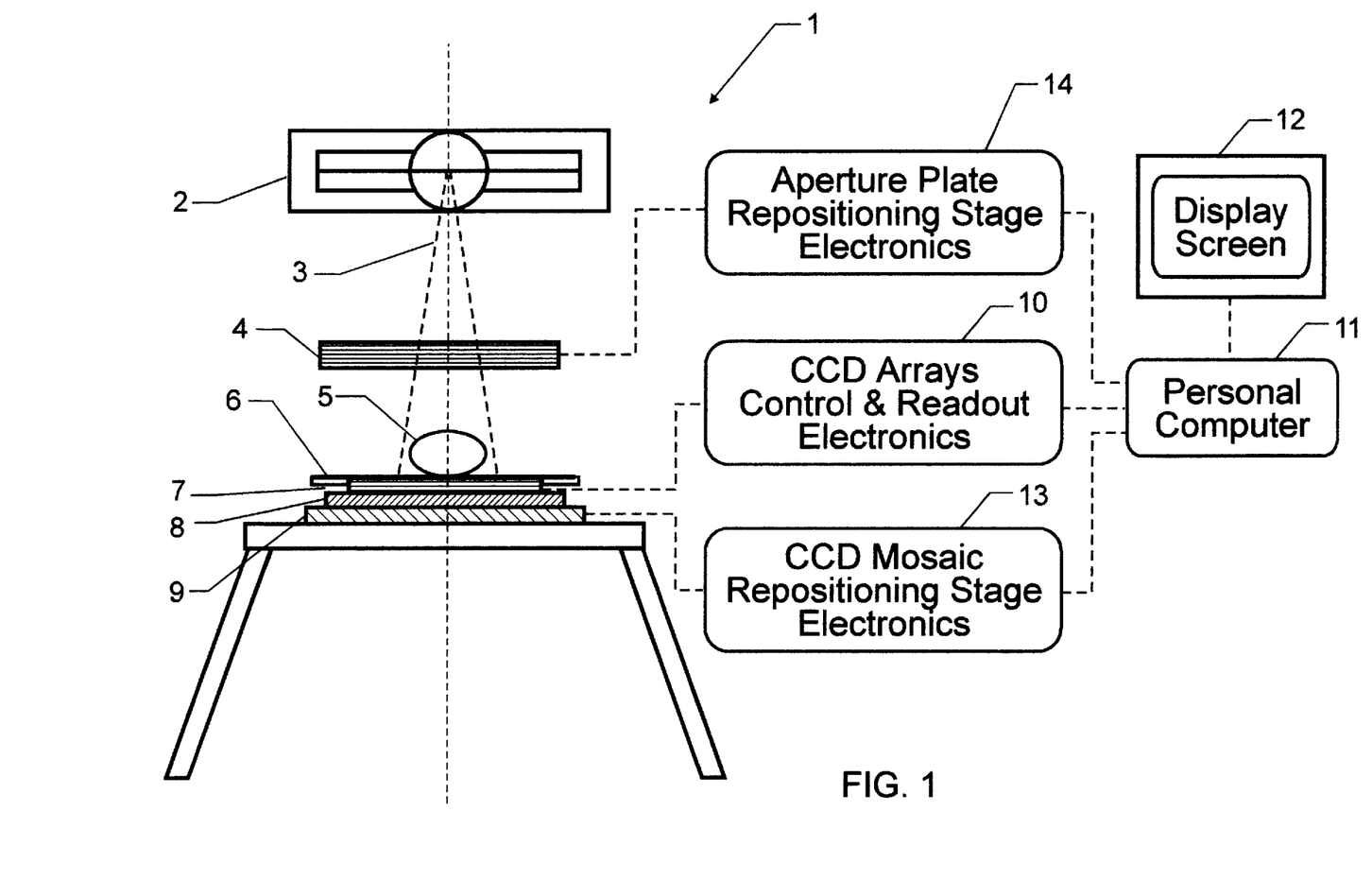
FIG. 1 shows a schematic description of the mammographic system.

Referring now to FIG. 1, the mammography system is shown generally by number 1. X-ray tube 2 emits x-rays 3 through the aperture plate 4 then through the patient 5. Aperture plate 4 serves to decrease patient x-ray dose and to reduce scattering of the x-ray beam. A phosphorescent screen 6 converts the x-ray image into a visible light image. Optical fibers 7, which attach the phosphorescent screen 6 to the CCD arrays, then transmit the visible light image to a mosaic of CCD arrays 8, which converts the light image into digital data. The CCD/readout electronics subsystem 10, some of which are located directly on the platform 16 and some of which are located externally, are used to transfer this data into a personal computer 11 for storage. A mechanical repositioning stage 9 moves the mosaic of CCD arrays to a new position, and this process is repeated until the entire image is exposed. The personal computer 11 combines this data to produce data which corresponds to the entire x-ray image. This x-ray image is displayed on an image display 12. Repositioning stage 9 is driven by the CCD mosaic repositioning stage electronics 13, under the control of the personal computer 11. The aperture plate repositioning stage electronics 14 moves the aperture plate 4 in synchronism with the CCD repositioning stage 9, also under control of the personal computer 11.

Sensor means

Figure 2A:
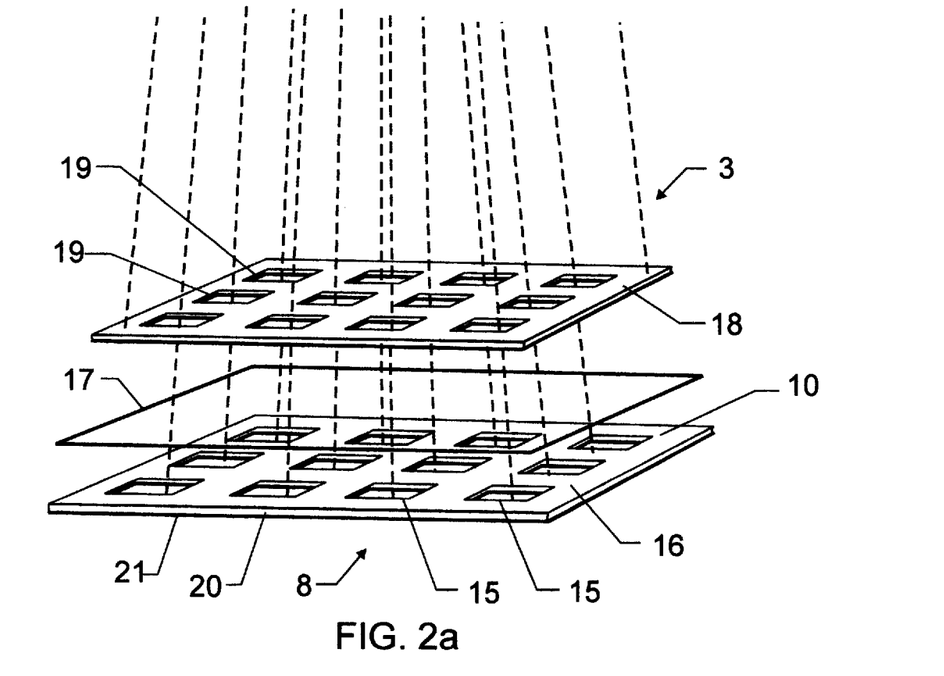
FIG. 2a shows a CCD mosaic.
Figure 2B:
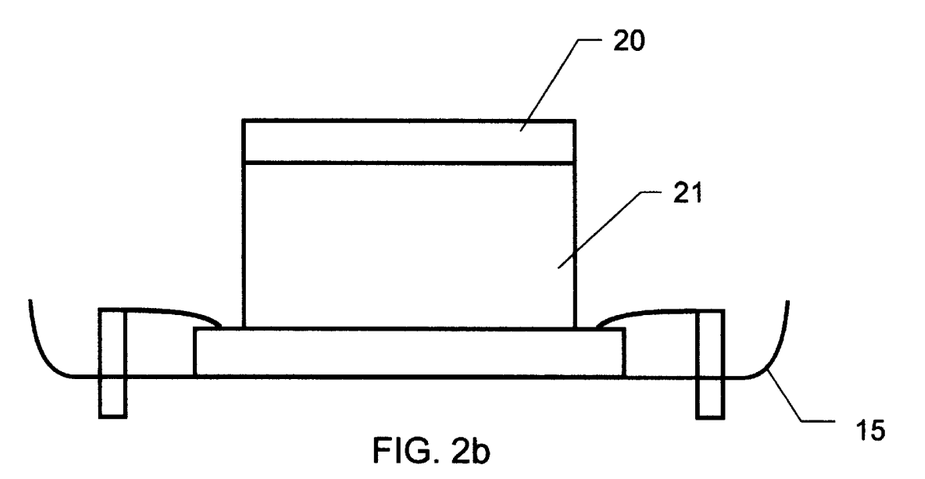
FIG. 2b shows a CCD imager with phosphor and fiber bundle.
Figure 3:
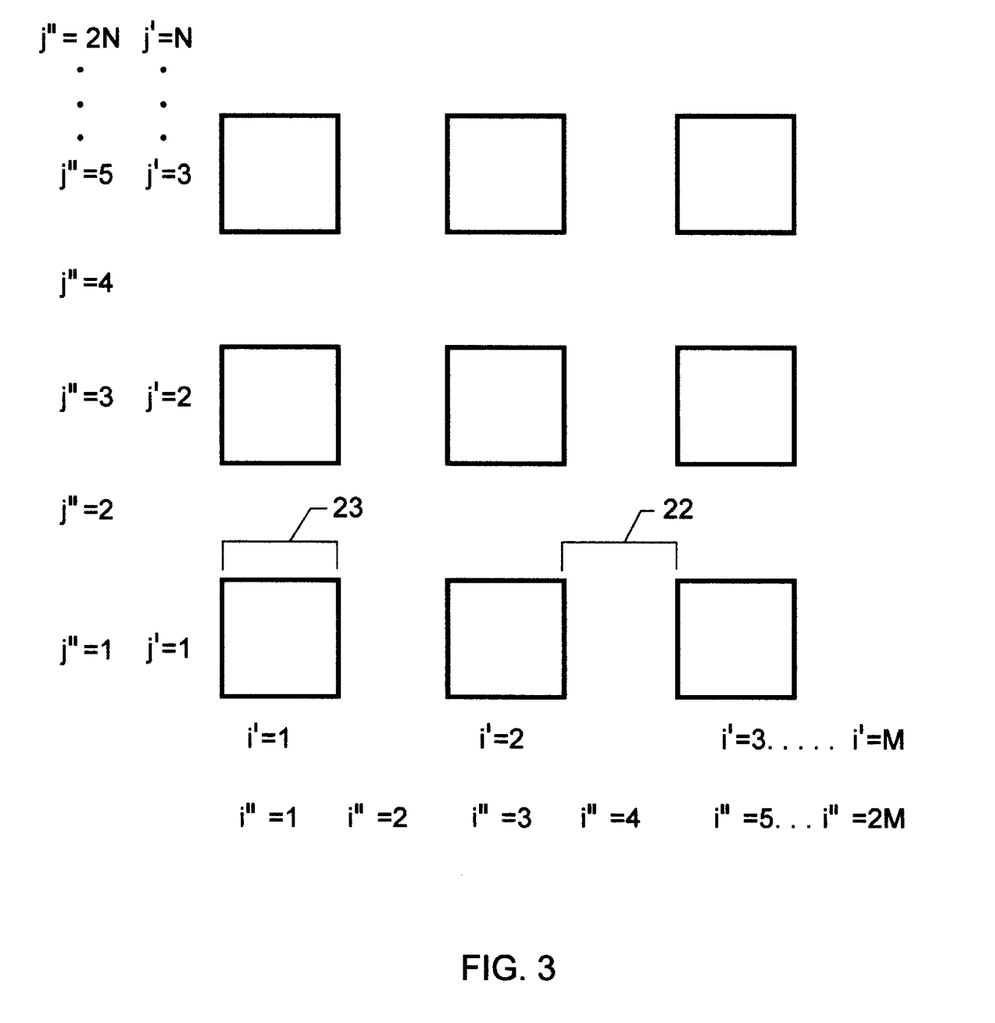
FIG. 3 shows arrangement of CCD arrays on the platform where i', j' denote CCD arrays and i", j" denote sub-images acquired by CCD arrays in various positions.

Referring now to FIGS. 2a and 2b, CCD mosaic 8 consists of CCD arrays 15 mounted onto a carrier platform 16. FIG. 3 shows that the length 22 between neighboring arrays is equal to the length 23 of one side of a square array. However, the arrays can have any shape and length so long as they are separated by a distance equal to the dimension of the arrays along each axis of motion minus an allowance for overlap of approximately 10 pixels between sub-images generated by each CCD in both directions. With this detector geometry, a single x-ray exposure will result in an image with gaps. These gaps in the image are removed by using multiple x-ray exposures. After each exposure, the platform 16 which carries the mosaic 8 of CCD arrays 15 is rapidly and accurately repositioned with respect to the patient 5 along two orthogonal axes. The repositioning can be accomplished with commercial mechanical stages.

The mosaic 8 is repositioned rapidly in order to minimize the effects of patient movement between exposures. The movement of the mosaic 8 is facilitated by the presence of an x-ray transparent plastic spacer plate 17 located between the patient 5 and the surface of the CCD mosaic 8.

Forty-eight 1024×1024 pixel CCD arrays, each measuring 15 mm×15 mm, are fixed to a 24 cm wide by 18 cm high carrier platform. FIG. 3 shows that the length 22 between neighboring arrays is equal to the length 23 of one side of a square array. However, the arrays can have any shape and length, so long as they are separated by a distance equal to the dimension of the arrays along each axis of motion minus an allowance for overlap of approximately 10 pixels between sub-images generated by each CCD in both directions.

In order to provide a complete and contiguous image, the mosaic 8 is repositioned three times, as shown in FIGS. 4 through 7. Four x-ray exposures are made. After the first exposure, the mosaic 8 is moved along the x axis a length 22, then a second exposure is made. The mosaic 8 is then moved along the y axis by a length 22, followed by a third exposure. The mosaic is then moved along x axis in a direction opposite the first motion. A final exposure then completes the data acquisition sequence.

In an alternate embodiment, the detector mosaic has 48 individual CCD arrays are assembled into a 6×8 mosaic with less than 5 mm wide gaps (where the gap width is W) between the individual CCD arrays. The repositioning takes place along a diagonal direction of the array. After a first x-ray exposure, the entire mosaic of CCD arrays is mechanically repositioned with respect to the human subject to be imaged. The mosaic is first moved in a diagonal direction by $\sqrt{2}$ W mm (simultaneously, W mm upward and W mm sideways). Then a second exposure is made followed by a second movement of the detectors along the same diagonal direction. A third exposure completes the data acquisition sequence. As in the preferred embodiment, the aperture shield is moved in synchronism with the mosaic of CCD arrays.

Shielding means

These multiple x-ray exposures can result in a high dose of radiation to the patient. In order to reduce the amount of x-ray exposure and scatter, a metal aperture plate 18 as shown in FIG. 2a is interposed between the x-ray source 2 and the patient 5. The plate 18 has a mosaic of apertures 19 which are in exact alignment with the mosaic 8 of detector arrays 15. This aperture plate 18 is moved by a second repositioning device in synchronism with the mosaic 8 detector arrays 15.

The patient 5 receives a small amount of additional exposure from x-rays in a narrow borderline area that surrounds each array. However, appropriate configuring of the instrument allows this area to be kept to less than 7.5 percent. Thus, patient dosage is increased by this percentage.

Scatter Reduction

The aperture plate provides a significant reduction in x-ray scattering, which results in improved image contrast. Table 1 shows scatter as a function of compression and Bucky grid use based on 15–20 keV x-ray properties. The instrument configuration for the CCD mosaic technique allows easy adaptation of a screen film type Bucky grid subsystem for scatter control.

TABLE 1

| S/P values | 3.0 cm Compression | 4.5 cm Compression |
| --- | --- | --- |
| With Bucky Grid | Screen Film: 0.14 | Screen Film: 0.26 |
|  | This device: 0.05 | This device: 0.09 |
| W/O Bucky Grid | Screen Film: 0.40 | Screen Film: 0.75 |
|  | This device: 0.14 | This device: 0.27 |

Scatter reduction yields better contrast ratios and thus enhanced lesion detectability. For a performance comparison consider Bucky grid equipped film systems. With 3 cm breast compression they typically are capable of a Scatter to Primary (S/P) ratio in the range from 0.10 to 0.15. For the present invention, the Table shows a comparable S/P ratio of 0.14 for 3 cm compression without a grid.

However, this system has a dose penalty of just under 7.5 percent, as a result of border line area considerations discussed above, compared with an approximately 100 percent dose increase required for the Bucky grid which is generally used by film systems. A trade off analysis which considers contrast shows that the present invention can achieve identical lesion detectability with 45 to 50 percent less radiation dosage, depending on compression. This result clearly shows the advantage of the present invention, which can operate without a Bucky grid because of the inherent scatter rejection of the aperture plate.

Repositioning means

The synchronous repositioning of the mosaic 8 of detectors 15 and aperture plate 18 is accomplished with two separate 2 axis mechanical repositioning devices with electronic coupling, such as the 800000 series precision positioning stage from Parker Hannifin. Stage movement of the repositioning devices is controlled by a Computermotor Plus closed loop brushless servo-motor system from Parker Hannifin. A step-motor system may also be used. Direct access programming allows the user to adjust all parameters via the RS232 interface.

Appropriate phasing of the independent motions of the detector mosaic 8 and the aperture plate 18 ameliorates mechanical vibrations to the instrument. One method of reducing vibrations is to move the aperture plate 18 in the direction opposite to the motion of the detector mosaic 8.

Exposure means

Each CCD array 15 in the mosaic 8 is coupled to the x-ray image 3 by using a phosphor screen 20 which converts the x-ray image into visible light. As shown in FIG. 2b, the screen 20 is separated from the CCD array 15 by a fiber optic bundle 21 with unity magnification. The main purpose of the fiber optic bundle 21 is to absorb a majority of the x-rays that are not stopped by the scintillating screen 20. This will prevent noise problems which result from x-rays contacting the CCD arrays. This unity magnification of the bundle 21 will avoid contrast degradation that is usually associated with an optical fiber taper.

Data Transfer means and Data storage means

In the time period between the radiation exposures, while the mosaic of detectors is being repositioned, the data is transferred from the CCD arrays 15 into the personal computer 11. When a data clocking speed of 1.5 million pixels per second is used, approximately 280 milliseconds will be required to transfer the data from the pixels into computer memory.

The transfer of the image data from the CCD arrays 15 to a data storage means such as a standard personal computer (PC) 11 can be accomplished through a process called binning. The scintillator screen resolution of 16–18 line-pairs/mm will be the limit of the overall system spatial resolution. The available CCD pixel size of 15 by 15 microns is much larger than needed to match the screen resolution. Therefore, the output of four adjacent pixels (2 by 2 pixels) can be simultaneously clocked and electronically combined without any degradation of the system resolution.

This binning of data offers several important advantages. First, if one of the four adjacent CCD array pixels is defective, binning can still deliver an image without drop out. Thus, lower grade and less expensive CCD arrays can be used.

Second, binning reduces the required total computer memory. This is a major point, because even with binning, recording a complete 18 cm by 24 cm image presently requires 75 Mbytes. An additional 25 Mbytes of memory will be needed for data processing, image manipulation, and system management. Much of this data can be swapped from hard disk or other permanent storage medium.

Third, binning reduces the information transfer time. Binning is partly accomplished in analog fashion by performing two parallel transfers prior to each readout of the serial register of the CCD. This allows the required CCD readout time to be reduced by one half Short read out times are crucial in order to minimize the image blurring effects of patient motion. The CCD contents from each of the first three exposures is read into computer memory coincident in time with each of the corresponding three detector repositioning times that follow exposure.

A readout rate is chosen for parallel and serial binned pixels. The upper and lower serial registers and read out amplifiers available with the Loral Inc., CCD are used. The rate is set at less than the maximum rate available for this CCD in order to improve the CCD charge transfer efficiency and the CCD amplifier read noise. The requirements on the CCD parallel register drivers, which are adversely affected by capacitive loading at high clock rates are also relaxed. This approach requires an additional analog to digital converter and its electronics for each CCD.

Data Combining means (Image Reconstruction)

The software manipulations needed to reconstruct a seamless image require two steps. First, a simple coordinate repositioning of the stored data is done in order to translate the stored data which was generated after each exposure by the distance the CCD arrays had been moved prior to each exposure.

Second, a linear scale factor correction method for pixel to pixel response and radiation source intensity variations is performed. A linear scale factor data array is derived using reference image information. A reference image is generated and recorded by the same image producing method described above. A correction data array is then created by dividing the output of each individual pixel by the output average of the entire array. For all subsequent testing, the raw images are normalized using this linear scale factor data array.

Image reconstruction

Image acquisition/Processing Procedure

1. Obtain Offset/Dark Current Subtraction Values a. Simultaneously and independently integrate all CCD arrays under dark conditions for time $\tau_1$. Store results for array at position i',j' in array variables $DA_{i',j',k,l}$, where k,l are indices of pixels on each array.

b. Obtain new dark exposure for each array and store results as $DS_{i',j',k,l}$ c. Update running total of dark exposure data:

$$DA_{i',j',k,l} = DA_{i',j',k,l} + DS_{i',j',k,l}$$

d. Repeat steps b and c $N_d$ more times—$N_d$ typically ranges from 5–10 e. Compute average dark level for each array:

$$DA_{i',j',k,l} = \frac{DA_{i',j',k,l}}{(N_d + 2)}$$

2. Obtain Non-Uniformity Correction Values a. Simultaneously and independently integrate all CCD arrays under exposure from clinical x-ray source with no subject present for time $\tau_i$ at a dose that produces a spatially uniform ($\leq 2\%$ variation) signal level of 80%–90% of pixel full well capacity. Store results in array variables $RA_{i',j',k,l}$ b. Obtain new exposure under same conditions and store results as $RS_{i',j',k,l}$ c. Update running total of non-uniformity correction data:

$$RA_{i',j',k,l} = RA_{i',j',k,l} + RS_{i',j',k,l}$$

d. Repeat steps b and c $N_r$ more times—$N_r$ typically ranges from 15–30 e. Compute average non-uniformity response of each array:

$$RA_{i',j',k,l} = \frac{RA_{i',j',k,l}}{(N_r + 2)}$$

f. Compute difference frame between dark and exposed response for each array:

$$RA_{i',j',k,l} = DA_{i',j',k,l} - RA_{i',j',k,l}$$

g. Compute average response of all arrays:

$$\overline{A} = \frac{\left( \sum_{i'=1}^{M} \sum_{j'=1}^{N} \sum_{k=0}^{N_{pix}-1} \sum_{l=0}^{N_{pix}-1} RA_{i',j',k,l} \right)}{(N_{pix}^2)(MN)}$$

where $N_{pix}$ = the number of array pixels in each dimension h. Compute correction factor arrays:

$$CORR_{i',j',k,l} = \left( \frac{\overline{A}}{RA_{i',j',k,l}} \right)$$

i. Clear variables $RS_{i',j',k,l}$, $RA_{i',k',k,l}$, and $DS_{i',j',k,l}$

3. Acquire Clinical Image a. Position subject between mosaic and x-ray source b. Simultaneously and independently integrate all CCD arrays for time $\tau_i$ with appropriate clinical x-ray dose. Store results for each sub-image in array variables $PV1_{i',j',k,l}$ (See FIG. 4)

c. During readout in step b, translate mosaic and aperture shield such that an exposure can be acquired at position indicated by FIG. 5. Maintain approximately 10 pixels at overlap between exposures from sub-image in each direction d. Acquire second exposure and store results in array variables $PV2_{i',j',k,l}$ e. translate a mosaic and aperture plate to allow acquisition of sub-image in position indicated by FIG. 6.

f. Acquire third exposure and store results in array variables $PV3_{i',j',k,l}$ g. Translate mosaic and aperture plate to allow acquisition at sub-image in position indicated by FIG. 7.

h. Acquire fourth exposure and store results in array variables $PV4_{i',j',k,l}$ 4. Process Data and Reconstruct Image a. Correct sub-image data for dark response and non-uniformity:

$$PV1_{i',j',k,l} = CORR_{i',j',k,l}(DA_{i',j',k,l} - PV1_{i',j',k,l})$$

$$PV2_{i',j',k,l} = CORR_{i',j',k,l}(DA_{i',j',k,l} - PV2_{i',j',k,l})$$

$$PV3_{i',j',k,l} = CORR_{i',j',k,l}(DA_{i',j',k,l} - PV3_{i',j',k,l})$$

$$PV4_{i',j',k,l} = CORR_{i',j',k,l}(DA_{i',j',k,l} - PV4_{i',j',k,l})$$

b. Initialize sub-image counters:

i'=1; j'=1 c. Compute reconstructed image pixel values and store in array PV $$PV\left( k' + \sum_{i''=0}^{2i'-2} N_{x_{i''}}, l' + \sum_{j''=0}^{2j'-2} N_{y_{j''}} \right) = PV1_{i',j',k,l'}$$

$$PV\left( k' + \sum_{i''=0}^{2i'-1} N_{x_{i''}}, l' + \sum_{j''=0}^{2j'-2} N_{y_{j''}} \right) = PV2_{i',j',k,l'}$$

$$PV\left( k' + \sum_{i''=0}^{2i'-1} N_{x_{i''}}, l' + \sum_{j''=0}^{2j'-1} N_{y_{j''}} \right) = PV4_{i',j',k,l'}$$

where $N_{x_0} \equiv 0, N_{y_0} \equiv 0$ $$PV\left( k' + \sum_{i''=0}^{2i'-2} N_{x_{i''}}, l' + \sum_{j''=0}^{2j'-1} N_{y_{j''}} \right) = PV3_{i',j',k,l'}$$

d. Increment i' by 1 until i'=M e. Increment j' by 1 until j'=N f. Display image array PV using appropriate gray scales For purposes of the preceding steps, $$k' = k - \frac{N_{ovx}}{2}$$

$$\text{for } \frac{N_{ovx}}{2} \leq k \leq N_{pix} - \frac{N_{ovx}}{2}$$

$$l' = l - \frac{N_{ovy}}{2}$$

$$\text{for } \frac{N_{ovy}}{2} \leq l \leq N_{pix} - \frac{N_{ovy}}{2}$$

Figure 4:
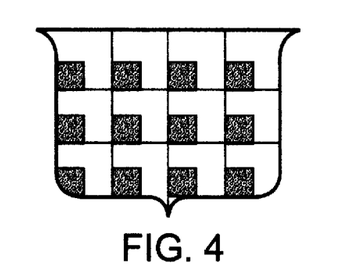
FIGS. 4 through 7 show the positions of the arrays which are needed to convert the entire x-ray into digital data.
Figure 5:
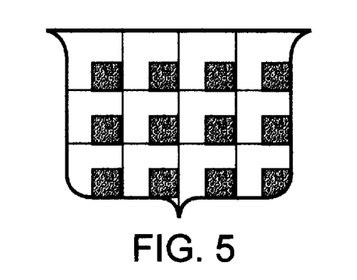
Figure 6:
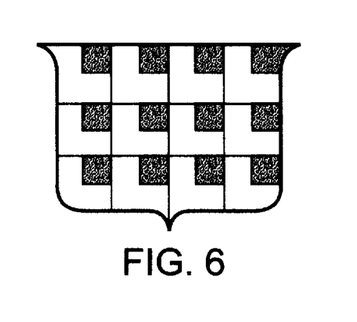
Figure 7:
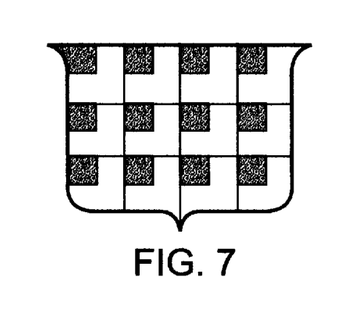

$N_{ovx}$≡ the approximate number of pixels overlap in sub-images in the X direction between exposures
$N_{ovy}$≡ the approximate number of pixels overlap in sub-images in the Y direction between exposures
$N_{x,i''}$≡ the sizeof the pixel offset along the X direction between sub-images at positions i" and i"+1, for the CCD sub region defined by:

$$\frac{N_{ovx}}{2} \leq k \leq N_{ovx} - \frac{N_{ovx}}{2}$$

$$\frac{N_{ovy}}{2} \leq l \leq N_{ovy} - \frac{N_{ovy}}{2}$$

between positions described in FIGS. 4 and 5 for sub-image at index i"
$N_{y,j''}$≡ the size of the pixel offset along the Y direction between sub-images at positions j" and j"+1, for the CCD sub region defined by:

$$\frac{N_{ovx}}{2} \leq k \leq N_{ovx} - \frac{N_{ovx}}{2}$$

$$\frac{N_{ovy}}{2} \leq l \leq N_{ovy} - \frac{N_{ovy}}{2}$$

between positions described in FIGS. 5 and 6 for sub-image at index j"
offsets $N_{x,j''}$ and $N_{y,j''}$ are obtained by taking the test image incorporating grid lines crossing boundaries between all sub-images along directions orthogonal to boundary and adjusting values until r.m.s. difference between cross sections on both sides of boundaries are minimized.
Aperture sizes on aperture shield shall be set to produce 5–10% overlap in illuminated regions along each linear dimension between sub-images. The process assumes all CCD's have the same rotational orientation to within $$\Delta\theta \leq \frac{1}{N_{pix}}$$

where $\Delta\theta$ is the angle of rotation.

While preferred embodiments have been described in detail, numerous modifications and changes may be made within the principles of the invention which is to be limited only by the appended claims.

We claim:

1. An apparatus for producing a digital mammogram of a patient comprising:
   a CCD/readout electronics subsystem having a plurality of CCD arrays for converting radiation into digital image data,
   means for exposing the CCD/readout electronics subsystem to a portion of a radiated image a plurality of times,
   means for repositioning the CCD/readout electronics subsystem after each exposure until the entire radiated image is exposed to the CCD/readout electronics subsystem,
   means for transferring data generated at each exposure to a data storage means, and
   means for combining the stored data which was generated at each exposure to form data corresponding to the radiated image.

2. An apparatus according to claim 1 where the means for exposing includes:
   a phosphor screen for converting an x-ray image into visible light, and
   a fiber optic bundle connected to the phosphor screen and the CCD/readout electronics subsystem.

3. An apparatus according to claim 1 further comprising an x-ray source,
   an x-ray shielding means having a plurality of apertures aligned such that each CCD array is exposed to x-rays over a selected imaging region with the x-ray shielding means placed between the x-ray source and the patient, and
   means for repositioning the x-ray shielding means after each exposure.

4. An apparatus according to claim 1 where the data storage means is a personal computer.

5. An apparatus according to claim 1 further comprising a display means for displaying data corresponding to the radiated image.

6. An apparatus according to claim 1 further comprising an x-ray transparent plate located above the CCD arrays.

7. A method of producing a digital mammogram comprising the steps of:
   exposing a CCD/readout electronics subsystem having a plurality of CCD arrays for converting radiation into digital data to a portion of a radiated image a plurality of times,
   repositioning the CCD/readout electronics subsystem after each exposure until the entire radiated image is exposed to CCD/readout electronics subsystem,
   transferring data generated at each exposure to a data storage means, and
   combining the stored data which was generated at each exposure to form data corresponding to the radiated image.

8. A method according to claim 7 comprising the further step of
   placing an x-ray shielding means having a plurality of apertures between an x-ray source and the patient, and
   repositioning the shielding means after each exposure such that each CCD array is exposed to x-rays over a selected imaging region.

9. A method according to claim 7 where the data transferred from a plurality of adjacent pixels located on the CCD arrays to the data storage means is simultaneously clocked and electronically combined.

10. A method according to claim 7 where the step of combining the stored data comprises:
    coordinate repositioning of the stored data which was generated at each exposure by the extent the CCD arrays had been moved prior to each exposure, and
    performing a linear scale factor correction method for variations in pixel to pixel response and radiation source intensity variations.

11. A method according to claim 10 where the linear scale factor correction method comprises the steps of:

generating and recording reference image data, creating a correction data array by dividing the digital data output of each pixel by the output average of the entire array, and normalizing all subsequent data by using the correction data array.

12. A digital mammography device comprising:

x-ray means having a plurality of x-ray point sources for creating a radiated image, CCD/readout electronics subsystem having a plurality of CCD arrays for converting radiation into digital data, means for exposing the CCD/readout electronics subsystem to a portion of the radiated image a plurality of times, means for sequentially energizing the point sources after each exposure until the entire image is exposed to the CCD/readout electronics subsystem, means for transferring data which was generated at each exposure to a data storage means, and means for combining the stored data which was generated at each exposure to form data corresponding to the radiated image.

13. A device according to claim 12 where the x-ray means comprises a plurality of x-ray devices located at the plurality of point sources.

14. A device according to claim 12 where the x-ray means comprises one x-ray device which is placed at an initial point source and moved to a subsequent point source after each exposure.

15. A device according to claim 12 where the means for exposing includes:

a phosphor screen for converting the x-ray image into a visible light image, and a fiber optic bundle connected to the phosphor screen and the CCD/readout electronics subsystem.

16. An device according to claim 12 further comprising:

an x-ray source, an x-ray shielding means having a plurality of apertures aligned such that each CCD array is exposed to x-rays over a selected imaging region with the x-ray shielding means placed between the x-ray source and the patient, means for repositioning the lead plate after each exposure, and an x-ray transparent plate located above the CCD arrays for facilitating movement of the CCD/readout electronics subsystem.

17. A device according to claim 12 where the data storage means is a personal computer.

18. A device according to claim 12 further comprising means for displaying data corresponding to the radiated image.

19. A device according to claim 12 further comprising means for three dimensional processing of data corresponding to the radiated image.

20. A method of producing a digital mammogram comprising the steps of:

exposing a CCD/readout electronics subsystem having a plurality of CCD arrays for converting radiation into digital data to a portion of a radiated image a plurality of times, sequentially energizing a plurality of x-ray point sources after each exposure until the entire image is exposed to the CCD/readout electronics subsystem, transferring data generated at each exposure to a data storage meab ns, and combining the stored data which was generated at each exposure to form data corresponding to the radiated image.

21. A method according to claim 20 comprising the further step of:

placing an x-ray shielding means having a plurality of apertures between an x-ray source and the patient: and repositioning the x-ray shielding means after each exposure such that each CCD array is exposed to x-rays over a selected imaging region.

22. A method according to claim 20 where the data transferred from a plurality of adjacent pixels located on the CCD arrays to the data storage means is simultaneously clocked and electronically combined.

23. A method according to claim 20 where the step of combining the stored data comprises:

coordinate repositioning of the stored data which was generated at each exposure by the distance the CCD arrays had been moved prior to each exposure, and performing a linear scale factor correction method for variations in pixel to pixel response and radiation source intensity variations.

24. A method according to claim 23 where the linear scale factor correction method comprises the steps of:

generating and recording reference image data, creating a correction data array by dividing the digital data output of each pixel by the output average of the entire array, and normalizing all subsequent data by using the correction data array.

25. A method according to claim 23 comprising the further step of performing three dimensional triangulations.

26. A method according to claim 20 comprising the further step of three dimensional image processing.

* * * * *